(12) United States Patent
Lee et al.

(10) Patent No.: US 9,178,129 B2
(45) Date of Patent: Nov. 3, 2015

(54) GRAPHENE-BASED FILMS IN SENSOR APPLICATIONS

(71) Applicant: The Trustees of the Stevens Institute of Technology, Hoboken, NJ (US)

(72) Inventors: Woo Young Lee, Ridgewood, NJ (US); Linh Tung Le, New York, NY (US); De Kong, Wood-Ridge, NJ (US)

(73) Assignee: THE TRUSTEES OF THE STEVENS INSTITUTE OF TECHNOLOGY, Hoboken, NJ (US)

( * ) Notice: Subject to any disclaimer, the term of this patent is extended or adjusted under 35 U.S.C. 154(b) by 0 days.

(21) Appl. No.: 14/053,232

(22) Filed: Oct. 14, 2013

(65) Prior Publication Data

US 2014/0103298 A1 Apr. 17, 2014

Related U.S. Application Data

(60) Provisional application No. 61/713,872, filed on Oct. 15, 2012.

(51) Int. Cl.
| | |
|---|---|
| *G01K 7/22* | (2006.01) |
| *H01L 37/00* | (2006.01) |
| *H01L 41/02* | (2006.01) |
| *G01N 33/48* | (2006.01) |

(Continued)

(52) U.S. Cl.
CPC ........ *H01L 37/00* (2013.01); *G01K 7/22* (2013.01); *G01K 15/005* (2013.01); *G01N 33/48* (2013.01); *H01L 41/02* (2013.01); *H01H 2047/025* (2013.01)

(58) Field of Classification Search
CPC .. G01K 7/22; G01K 15/005; H01H 2047/025
See application file for complete search history.

(56) References Cited

U.S. PATENT DOCUMENTS

| 4,772,924 A | 9/1988 | Bean et al. |
| 4,903,101 A | 2/1990 | Maserjian |

(Continued)

FOREIGN PATENT DOCUMENTS

| WO | 2012073998 A1 | 6/2013 |
| WO | 2013119295 | 8/2013 |

OTHER PUBLICATIONS

Le, "Inkjet-Printed Graphene for Flexible Micro-Supercapacitors", IEEE International Conference on Nanotechnology, Aug. 15-18, 2011.*

(Continued)

*Primary Examiner* — John C Ingham
(74) *Attorney, Agent, or Firm* — Greenberg Traurig, LLP (57) ABSTRACT

An environmental sensor comprises a graphene thin-film as an environmentally responsive material. Such graphene films exhibit negative temperature coefficients (NTC), resulting in rapid decreases in electrical resistance as temperature increases, as well as a much faster response time than any other NTC material reported in the literature. The graphene film is also mechanically stable under bending, and, therefore, can be adapted for use in a mechanical sensor or pressure sensor, because the electrical resistance of the graphene film changes upon deflection and/or changes in pressure. The electrical resistance of the graphene film also increases in response to increases in environmental humidity. The electrical resistance changes of the graphene film can also be used as a sensing mechanism for changes in chemical and biological parameters in the environment of the sensor.

2 Claims, 6 Drawing Sheets

(51) Int. Cl.
*G01K 15/00* (2006.01)
*H01H 47/02* (2006.01)

(56) References Cited

U.S. PATENT DOCUMENTS

| | | | |
|---|---|---|---|
| 5,238,868 | A | 8/1993 | Elman et al. |
| 6,813,064 | B2 | 11/2004 | John et al. |
| 7,167,355 | B2 | 1/2007 | Chen |
| 7,217,951 | B2 | 5/2007 | Krishna et al. |
| 7,387,253 | B1 | 6/2008 | Parker et al. |
| 7,550,755 | B2 | 6/2009 | Balkenende et al. |
| 7,628,928 | B2 | 12/2009 | Guerra |
| 7,830,926 | B1 | 11/2010 | Kim |
| 7,852,613 | B2 | 12/2010 | Ma et al. |
| 8,098,482 | B2 | 1/2012 | Clelland et al. |
| 8,206,469 | B2 | 6/2012 | Chiang et al. |
| 8,278,757 | B2 | 10/2012 | Crain |
| 8,455,842 | B2 | 6/2013 | Zhang |
| 8,697,485 | B2 | 4/2014 | Crain |
| 8,810,996 | B2 | 8/2014 | Lee et al. |
| 8,878,120 | B2 | 11/2014 | Patil et al. |
| 2003/0012249 | A1 | 1/2003 | Eisenbeiser |
| 2007/0215855 | A1 | 9/2007 | Kang |
| 2010/0207254 | A1 | 8/2010 | Jain et al. |
| 2011/0042813 | A1 | 2/2011 | Crain |
| 2011/0052813 | A1 | 3/2011 | Ho |
| 2011/0101309 | A1 | 5/2011 | Lin et al. |
| 2012/0007913 | A1 | 1/2012 | Jang |
| 2012/0121891 | A1 | 5/2012 | Kim |
| 2012/0128983 | A1 | 5/2012 | Yoon |
| 2012/0170171 | A1 | 7/2012 | Lee |
| 2012/0235119 | A1 | 9/2012 | Babich et al. |
| 2012/0244358 | A1 | 9/2012 | Lock |
| 2012/0255860 | A1 | 10/2012 | Briman et al. |
| 2012/0270205 | A1* | 10/2012 | Patel et al. .......................... 435/5 |
| 2013/0264011 | A1 | 10/2013 | Lin |
| 2013/0264192 | A1 | 10/2013 | Lin |
| 2013/0264193 | A1 | 10/2013 | Lin |
| 2013/0264307 | A1 | 10/2013 | Lin |
| 2013/0266729 | A1 | 10/2013 | Lin |
| 2014/0127584 | A1 | 5/2014 | Kim |
| 2014/0205841 | A1 | 7/2014 | Qiu et al. |
| 2014/0231002 | A1 | 8/2014 | Patil et al. |
| 2014/0321028 | A1 | 10/2014 | Lee et al. |

OTHER PUBLICATIONS

Kong, "Temperature Dependent Electrical Properties of Graphene Inkjet Printed on Flexible Materials", ACS Publications, Aug. 27, 2012.*
Akhavan, O. et al., Toxicity of graphene and graphene oxide nanowalls against bacteria, ACS Nano, 4 (2010) 5731-5736.
Bolotin, K. et al., Ultrahigh electron mobility in suspended graphene; Solid State Communications, 146 (2008) 351-355.
Bourlinos, A. et al., Graphite oxide: Chemical reduction to graphite and surface modification with primary aliphatic amines and amino acids, Langmuir, 19 (2003) 6050-6055.
Chen, Z. et al., Three-dimensional flexible and conductive interconnected graphene networks grown by chemical vapour deposition, Nature Materials, 10 (2011) 424-428.
Coleman, J.N., Liquid-Phase Exfoliation of Nanotubes and Graphene, Advanced Functional Materials, 19 (2009) 3680-3695.
Cote, L. et al., Flash Reduction and Patterning of Graphite Oxide and Its Polymer Composite, Journal of the American Chemical Society, 131 (2009) 11027-11032.
Dikin, D. et al., Preparation and characterization of graphene oxide paper, Nature, 448 (2007) 457-460.
Dreyer, D. et al., The chemistry of graphene oxide, Chemical Society reviews, 39 (2010) 228-240.
Dreyer, D. et al., From Conception to Realization: An Historical Account of Graphene and Some Perspectives for Its Future, Angewandte Chemie International Edition, 49 (2010) 9336-9344.

El-Kady, M. et al., "Laser Scribing of High-Performance and Flexible Graphene-Based Electrochemical Capacitors," Science, vol. 335, No. 6074, pp. 1326-1330, Mar. 2012.
Gao, X. et al., Hydrazine and thermal reduction of graphene oxide: Reaction mechanisms, product structures, and reaction design, Journal of Physical Chemistry C, 114 (2010) 832-842.
Hong, A. et al., "Graphene Flash Memory," ACS Nano 5 (10), 7812-7817 (2011).
Ferrari, A. et al., Inkjet-Printed Graphene Electronics; ACS Nano, vol. 6, No. 4, 2992-3006, (2012).
Kim, F. et al., Graphene oxide: Surface activity and two-dimensional assembly, Advanced Materials, 22 (2010) 1954-1958.
Kim, J. et al., Graphene oxide sheets at interfaces, Journal of the American Chemical Society, 132 (2010) 8180-8186.
Kong, D. et al., Temperature-Dependent Electrical Properties of Graphene Inkjet-Printed on Flexible Materials, Langmuir, ACS Publications, American Chemical Society, 28, (2012) pp. 13467-13472.
Lee, Y. et al., "Wafer-Scale Synthesis and Transfer of Graphene Films," Nano Letters 10 (2), 490-493 (2010).
Li, D. et al., Processable aqueous dispersions of graphene nanosheets, Nat Nano, 3 (2008) 101-105.
Li, X. et al., Large-Area Synthesis of High-Quality and Uniform Graphene Films on Copper Foils, Science, 324 (2009) 1312-1314.
Lin, Y. et al., "100-GHz Transistors from Wafer-Scale Epitaxial Graphene," Science, 327 (2010) p. 662.
Lin, Y. et al., "Wafer-Scale Graphene Integrated Circuit," Science 332 (6035), 1294-1297 (2011).
Luo, J. et al., Compression and Aggregation-Resistant Particles of Crumpled Soft Sheets, ACS Nano, 5 (2011) 8943-8949.
Luo, J. et al., Graphene oxide nanocolloids, Journal of the American Chemical Society, 132 (2010) pp. 17667-17669.
Novoselov, K. et al., Electric Field Effect in Atomically Thin Carbon Films, Science, 306 (2004) pp. 666-669.
Park, J. et al., Multi-scale graphene patterns on arbitrary substrates via laser-assisted transfer-printing process, Applied Physics Letters, vol. 101, No. 4, (2012) p. 043110-043110-4.
Park, S. et al., Chemical methods for the production of graphenes, Nat Nano, 4 (2009) 217-224.
Shao, G. et al., Graphene oxide: The mechanisms of oxidation and exfoliation, Journal of Materials Science, 47 (2012) 4400-4409.
Stankovich, S. et al., Synthesis of graphene-based nanosheets via chemical reduction of exfoliated graphite oxide, Carbon, 45 (2007) 1558-1565.
Stoller, M. et al., Graphene-Based ultracapacitors; Nano Letters, 8 (2008) 3498-3502.
Torrisi, F. et al., Inkjet-Printed Graphene Electronics, ACS Nano, vol. 6, No. 4, (2012) 2992-3006.
Wu, Z.S. et al., Graphene/metal oxide composite electrode materials for energy storage, Nano Energy, 1 (2012) 107-131.
Zangmeister, C.D., Preparation and evaluation of graphite oxide reduced at 220 c, Chemistry of Materials, 22 (2010) 5625-5629.
Zhang, Y. et al., Cytotoxicity effects of graphene and single-wall carbon nanotubes in neural phaeochromocytoma-derived pc12 cells, ACS Nano, 4 (2010) 3181-3186.
Zhang, Y. et al., "Direct imprinting of microcircuits on graphene oxides film by femtosecond laser reduction," Nano Today, vol. 5, (2010) pp. 15-20.
Zhu, Y. et al., Carbon-Based Supercapacitors Produced by Activation of Graphene; Science, 332 (2011) 1537-1541.
Havener, R. et al., Hyperspectral Imaging of Structure and composition in Atomically Thin Heterostructures; ACS Nano, 13 (2013) 3942-3946.
Ko, S. et al., Unconventional, Laser Based OLED Material Direct Patterning and Transfer Method; Organic Light Emitting Diode—Material, Process and Devices; Intech, ISBN: 978-953-307-273-9.
Lee, K. et al., Effect of Laser Beam Trajectory on Donor Plate in Laser Induced Thermal Printing Process; Journal of the Optical Society of Korea, vol. 15, No. 4, Dec. 2011, pp. 362-367.
Cho, S. et al., Enhanced efficiency of organic light emitting devices (OLEDs) by control of laser imaging condition; Organic Electronics 13 (2012) 833-839.

(56) References Cited

OTHER PUBLICATIONS

Olivares-Marín, M. et al., Cherry stones as precursor of activated carbons for supercapacitors; Materials Chemistry and Physics 114, 1, (2009) 223-227.

An, L. et al., Optical and Sensing Properties of 1-Pyrenecarboxylic Acid-Functionalized Graphene Films Laminated on Polydimethylsiloxane Membrane, American Chemical Society, vol. 5, No. 2, (2011), pp. 1003-1011.

Le, L. et al., Graphene supercapacitor electrodes fabricated by inkjet printing and thermal reduction of graphene oxide, Electrochemistry Communications, vol. 13, (2011), pp. 355-358.

Le, L. et al., Inkjet-Printed Graphene for Flexible Micro-Supercapacitors, IEEE International Conference on Nanotechnology, Aug. 15-18, 2011, Portland, Oregon, USA, pp. 67-71.

Huang, L. et al., Graphene-Based Conducting Inks for Direct Inkjet Printing of Flexible Conductive Patterns and Their Applications in Electric Circuits and Chemical Sensors, Nano Res, (2011) 9 pages.

Jacoby, M., Graphene Moves Toward Applications, www.cen-online.org, Nov. 21, 2011, pp. 10-15.

Jang, B.Z. et al., Processing of nanographene platelets (NGPs) and NGP nanocomposites: a review; Journal of Materials Science 43, 5092-5101, (2008).

Jang, B.Z. et al., Graphene-Based Supercapacitor with an Ultrahigh Energy Density; NanoLetters, 10, 4863-4868, (2010).

U.S. Appl. No. 14/327,716, filed Jul. 10, 2014.

U.S. Appl. No. 14/327,753, filed Jul. 10, 2014.

Zhou, M. et al., Controlled Synthesis of Large-Area and Patterned Electrochemically Reduced Graphene Oxide Films, Chem. Eur. J., 2009, 15, pp. 6116-6120.

Notice of Allowance mailed Jan. 22, 2015 in reference to U.S. Appl. No. 14/327,716.

Non-Final Office Action mailed Aug. 15, 2014 in reference to U.S. Appl. No. 14/327,716.

Non-Final Office Action mailed Dec. 6, 2013 in reference to U.S. Appl. No. 13/301,124.

Final Office Action mailed Jun. 25, 2014 in reference to U.S. Appl. No. 13/324,622.

\* cited by examiner

GRAPHENE-BASED FILMS IN SENSOR APPLICATIONS

CROSS-REFERENCE TO RELATED APPLICATIONS

The present application claims the benefit of U.S. Provisional Patent Application No. 61/713,872, filed on Oct. 15, 2012, the disclosure of which is incorporated by reference herein in its entirety.

STATEMENT REGARDING FEDERALLY SPONSORED RESEARCH

The technology disclosed herein was in part derived from research supported by the U.S. Government as part of Task Order #76 of Contract W15QKN-05-D-0011-0076 "Integrated Flexible Electronics and Energetics". The U.S. Government may have certain rights to the invention disclosed herein.

FIELD OF THE INVENTION

The present invention relates to the graphene thin films fabricated by inkjet printing of graphene oxide with subsequent reduction to graphene, and, more specifically to the use of such graphene thin films as electrical sensors for sensing temperature, humidity, mechanical stresses or strains, or chemical, biological species.

BACKGROUND OF THE INVENTION

Temperature sensors such as thermistors are used in various applications, such as in gas sensors or in battery packs for optimization of battery life. Temperature sensors have elements with temperature-dependent electrical resistances. The temperature-resistance coefficient (i.e., the change in resistance with change in temperature) is positive for platinum-based materials and negative for metal oxides and semiconductors (i.e., metal oxides and semiconductors exhibit negative temperature coefficients ("NTC")). Such sensor elements are typically fabricated in the form of discs and pellets. For advanced applications, NTC elements should maintain their properties over time (i.e., they should not age too quickly for long-term use), and should remain mechanically flexible. The mechanism of tracking the electrical resistance as response to environmental conditions can also be used in other sensing applications such as sensing mechanical strain or stress, pressure, humidity, or the chemical and biological species. Respectively, the corresponding changes in electrical resistance can be directly correlated to the mechanical strain or stress, relative humidity and concentrations of chemical or biological species in gas or liquid media.

SUMMARY OF THE INVENTION

In embodiments of the present invention, graphene thin films (also referred to herein as "graphene films") are used as NTC temperature sensing elements. In some embodiments of the invention, inks prepared by dispersing graphene oxide sheets in water are used to print micropatterns of graphene oxide on a variety of flexible substrates (e.g., polyethylene terephthalate (PET), or Kapton® polyimide membrane) using a commercial inkjet printer. In some such embodiments of the invention, the printed micropatterns are subsequently reduced to graphene in minutes using an infrared heat lamp at a temperature of about 220° C. The spacing between adjacent ink droplets and the number of printing layers deposited may be adjusted to tailor the graphene film's electrical resistance. The graphene film behaves as a NTC sensing element, wherein electrical resistance decreases rapidly as temperature increases, providing a faster response time than any other NTC material reported in the literature to date. The electrical properties of the graphene film are also stable under mechanical bending of the graphene film. Embodiments of the present invention may be prepared to provide selected mechanical properties useful for mechanical sensors.

BRIEF DESCRIPTION OF FIGURES

For a more complete understanding of the present invention, reference is made to the following detailed description of exemplary embodiments considered in conjunction with the accompanying drawings, in which.

DETAILED DESCRIPTION OF THE INVENTION

Graphene has received significant attention in a variety of technical fields because of its potential use in highly-flexible electrically-conductive films for applications such as optoelectronics, energy storage, environmental sensors, and biomedical devices. Inkjet printing of aqueous dispersions of graphene oxide sheets and their subsequent reduction to graphene for use as supercapacitor electrodes is described in U.S. Patent Application Publication No. 2012/0170171, published on Jul. 5, 2012, the disclosure of which is incorporated by reference herein in its entirety. A similar approach is used in embodiments of the present invention to fabricate graphene thin films which exhibit NTC behavior with high sensitivity to temperature changes and fast response time, enabling their use as writable, very thin, flexible, and transparent sensing elements.

Figure 1:
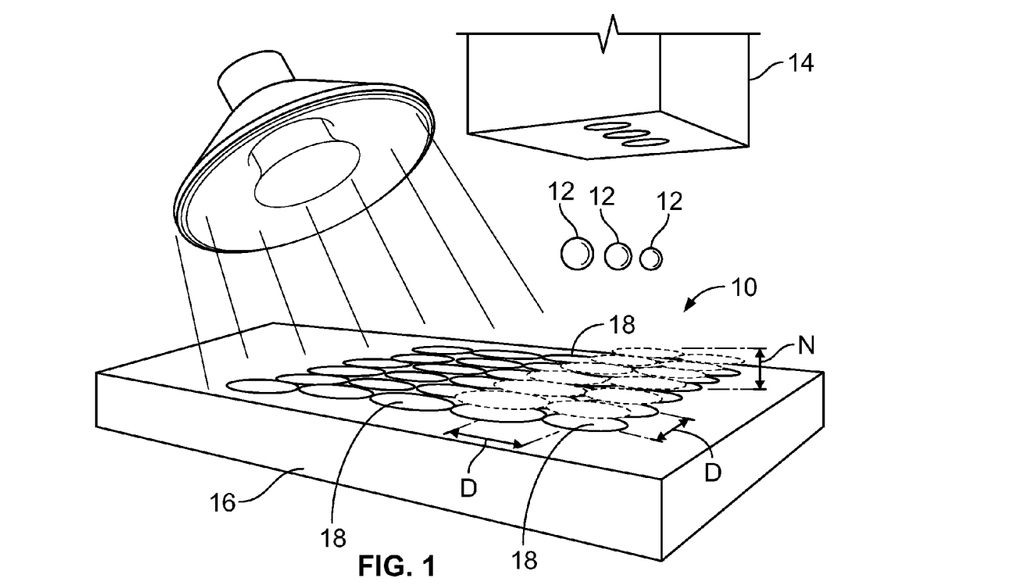
FIG. 1 is a schematic illustration of a process of forming flexible graphene micropatterns, according to a method of the present invention.

FIG. 1 is a schematic illustration of a process of forming flexible graphene micropatterns according to an embodiment of the present invention. The micropattern 10 is produced by depositing droplets 12 of an ink comprising graphene oxide dispersed in water from an inkjet printer head 14 onto current collectors (not shown) formed on a flexible substrate 16. Dot-like structures 18 are formed from the droplets 12 upon impact of the droplets 12 on the substrate 16. A commercial inkjet printer (e.g., a FUJIFILM Dimatix Materials Printer, DMP2800) may be used. In embodiments of the inventions, inks having a concentration of about 0.2% graphene oxide by weight may be used. The average lateral dimension of the graphene oxide sheets in an exemplary ink may be about 530 nm with about 35% of the graphene oxide sheets being smaller than 300 nm and about 30% of the graphene oxide sheets being larger than about 1000 nm. Sheets of graphene or graphene oxide are also referred to herein as "flakes". FIG. 1 also indicates the printing parameters of droplet spacing (D) and the number of layers printed (N) which affect the electrical properties of the graphene film.

Figure 2:
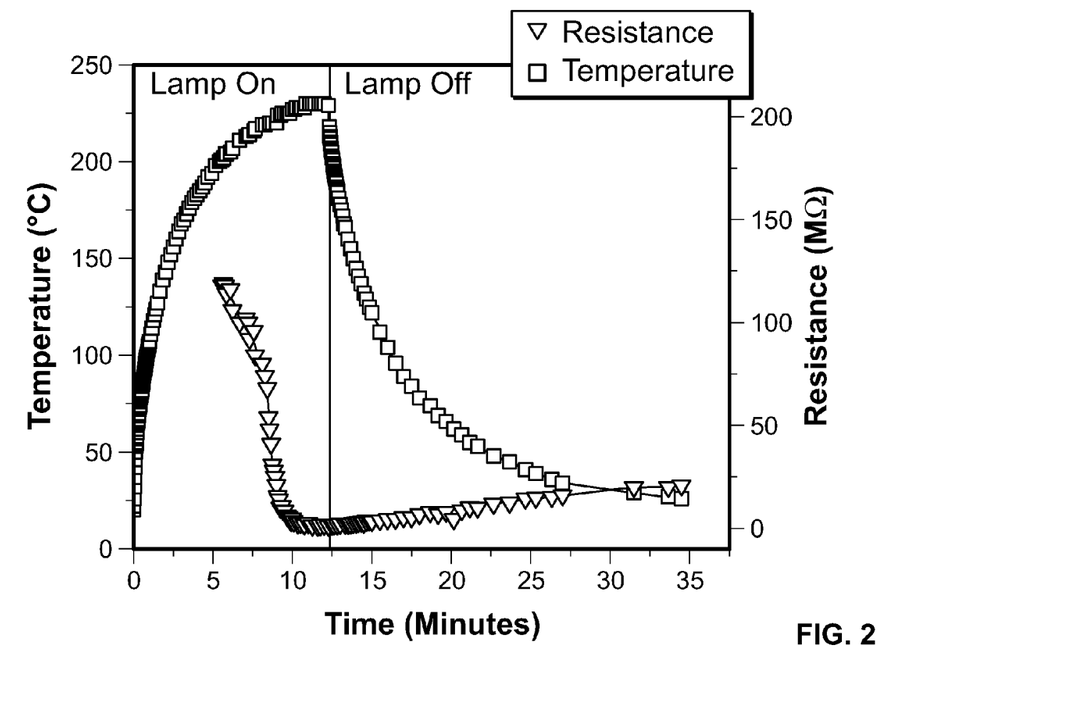
FIG. 2 is a plot of the changes in resistance of the micropattern as graphene oxide in the micropattern is converted to graphene using a heat lamp, according to an embodiment of the present invention.

In an exemplary embodiment of the invention, exposure to radiation from an infrared (IR) lamp reduced the graphene oxide in the printed micropatterns to graphene in about 10 minutes in an ambient room environment. As shown in FIG. 2, the substrate temperature rose to about 220° C. during a 12 minute exposure. The electrical resistance of the graphene film became measurable at about 5 minutes into the exposure period, and continuously decreased until it reached a steady state value after an exposure of about 10 minutes.

Figure 3:
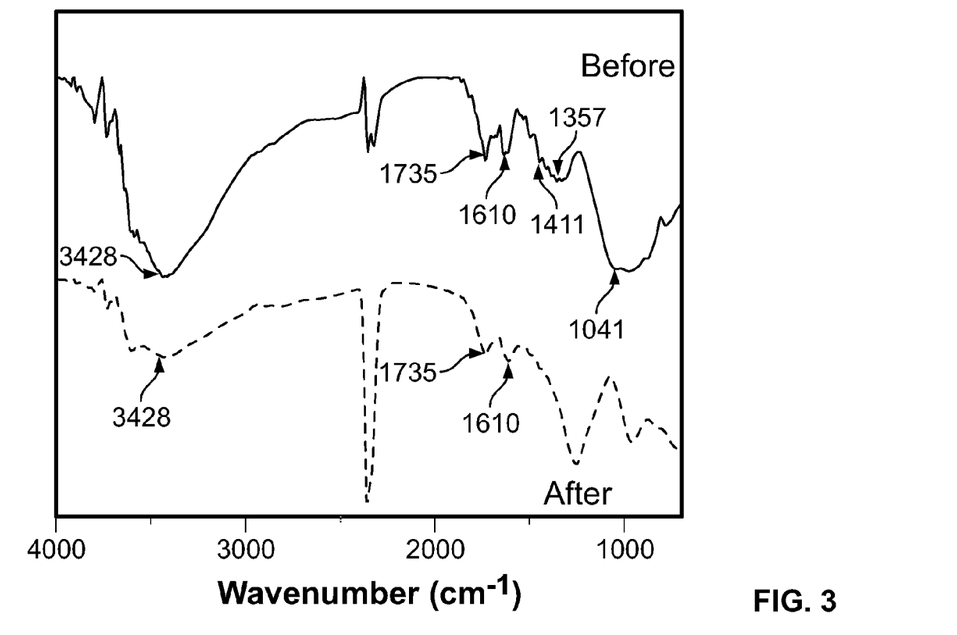
FIG. 3 presents plots of the Fourier transform infrared (FTIR) characteristics of graphene oxide sheets before (upper plot) and after (lower plot) reduction to graphene using an infrared heat lamp, according to an embodiment of the present invention.

The aforesaid changes in electrical properties of the printed film suggest that there is a significant removal of O—H functional groups from the exposed graphene oxide sheets during thermal reduction. FIG. 3 presents plots of the Fourier transform infrared (FTIR) characteristics of graphene oxide sheets before (upper plot) and after (lower plot) reduction to graphene using an infrared heat lamp, according to an embodiment of the present invention. Prior to thermal reduction, infrared absorption peaks characteristic of graphene oxide were present in the FTIR spectrum of the material including: (1) C=O stretching vibration at 1735 $cm^{-1}$, (2) O—H stretching vibration at 3428 $cm^{-1}$, (3) O—H deformation vibration at 1411 $cm^{-1}$, (4) aromatic C=C stretching vibration at 1610 $cm^{-1}$, and (5) alkoxy C—O stretching vibration at 1041 $cm^{-1}$. After thermal reduction, the 1411 $cm^{-1}$ and 1041 $cm^{-1}$ peaks disappeared, while the 3428 $cm^{-1}$ peak significantly decreased. The small 1735 $cm^{-1}$ peak still remained. However, the 1735 $cm^{-1}$ peak did not disappear, suggesting that the C=O stretching vibration of lactones was still present. The 1610 $cm^{-1}$ C=C peak was present, indicating that the $sp^2$ structure of carbon atoms was retained.

Figure 4:
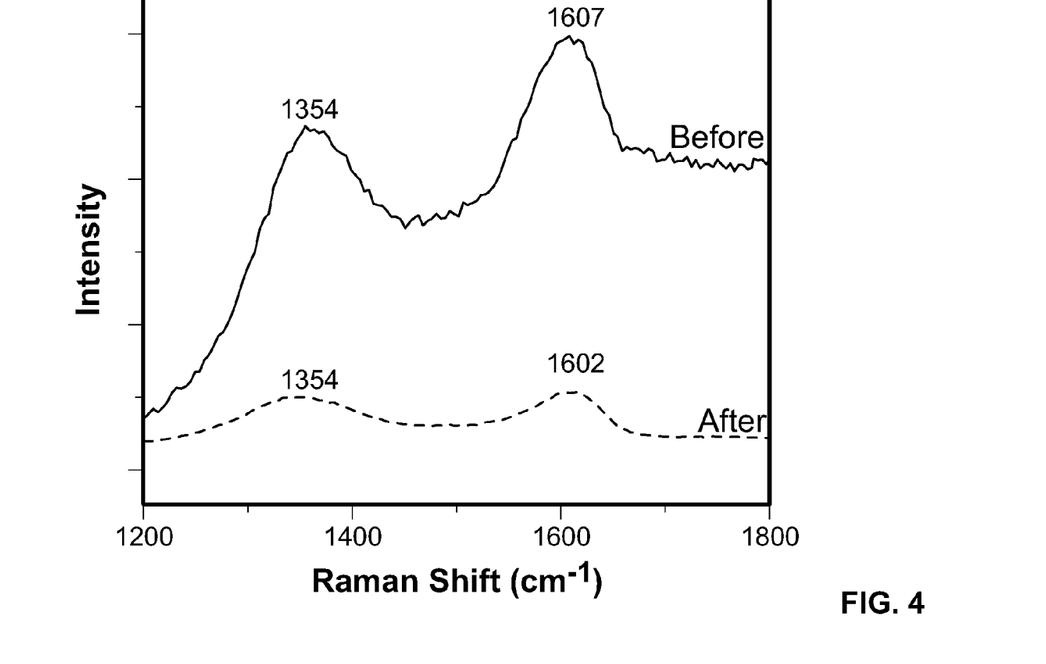
FIG. 4 presents Raman spectra of graphene oxide sheets before (upper spectrum) and after (lower spectrum) reduction to graphene using an infrared heat lamp, according to an embodiment of the present invention.

FIG. 4 presents Raman spectra of graphene oxide sheets before (upper spectrum) and after (lower spectrum) reduction to graphene using an infrared heat lamp, according to an embodiment of the present invention. Two prominent Raman peaks were observed before and after the thermal reduction step: (1) a G band (at about 1602 to 1607 $cm^{-1}$) corresponding to the first-order scattering of photons by $sp^2$ carbon atoms, and (2) a D band (at about 1354 $cm^{-1}$) arising from small domain-sized graphitic regions. The intensity ratio of the D to G bands ($I_D/I_G$) increased from 0.79 to 0.94 upon reduction. This change of ratio suggested that: (1) most of the oxygenated functional groups were removed from graphene oxide sheets by the reduction step, and (2) a $sp^2$ network was established. Upon reduction, the G band was slightly shifted to 1602 $cm^{-1}$ from 1607 $cm^{-1}$. However, the G and D bands of the reduced graphene oxide sheets present at 1602 $cm^{-1}$ and 1354 $cm^{-1}$ were considerably higher than those typically observed at 1575 $cm^{-1}$ and 1350 $cm^{-1}$ for chemically vapor deposited (CVD) graphene. These peak shifts indicate that a relative lack of $sp^2$ character and a remaining presence of some oxygenated functional groups, consistent with the FTIR results.

The FTIR and Raman results discussed with respect to FIGS. 3 and 4 suggest that thermal reduction using an infrared lamp is effective in reducing printed graphene oxide films to graphene films to a significant extent, but not completely. Reduction of graphene oxide by this method is particularly useful for films printed on thermally- and chemically-sensitive materials and devices. Also, the use of an infrared lamp is advantageous for easy integration with roll-to-roll, additive manufacturing since it only takes minutes to effect a suitable reduction, as opposed to the hours required for the thermal and chemical methods, without the need for controlled reduction environments and sophisticated equipment.

By varying printing parameters such as droplet spacing (D) and the number of layers printed (N), the electrical resistance and optical transparency of the graphene film can be tailored for specific applications. Variations in D and N are highly related to the morphology of the electrode patterns, and affect the electrical conductivity of the micropatterns by altering the number of available electron transport paths, as well as the availability of light-transmitting paths. In an exemplary embodiment of the invention, at D=20 μm, sheet resistance ($R_s$) decreased from about 12 MΩ/□ to about 0.3MΩ/□ upon increasing N from 2 to 5, and transparency of the film rapidly decreased from about 76% to about 45%. Optimization and control of the electrical resistance and optical properties can be used to achieve a desired purpose, whether for a temperature-sensing application or for an electrochemical sensing application, or even for other sensing applications.

In a demonstration of the performance of the printed graphene temperature-dependent film of an embodiment of the present invention, D=20 μm and N=2 were determined to be optimum printing parameters for producing a continuous morphology of a graphene printed on Kapton, with the film having $R_s$=12 MΩ/□ and a 76% transparency. This optoelectrical performance compares well with a printed graphene electrode that was produced by ultra-sonic exfoliation of a graphite powder and dispersal in organic solvent (see, e.g., Torrisi et al., Inkjet-Printed Graphene Electronics, *ACS Nano*, 2012, 6 (4), pp 2992-3006, which is incorporated by reference herein).

Figure 5:
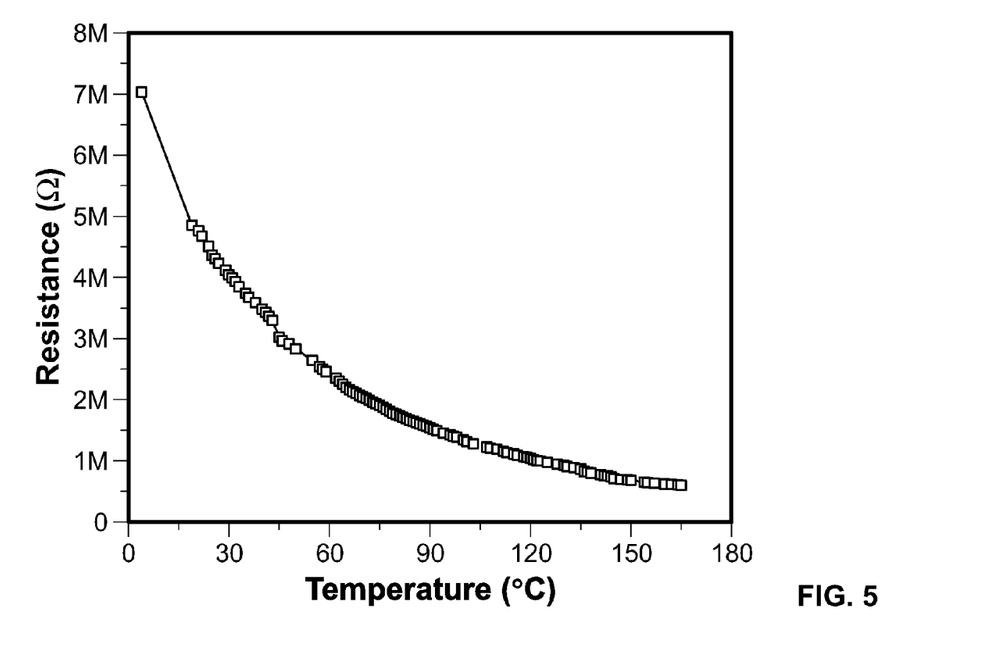
FIG. 5 is a plot of showing the temperature dependence of the electrical resistance of a graphene film prepared according to an embodiment of the present invention.
Figure 6:
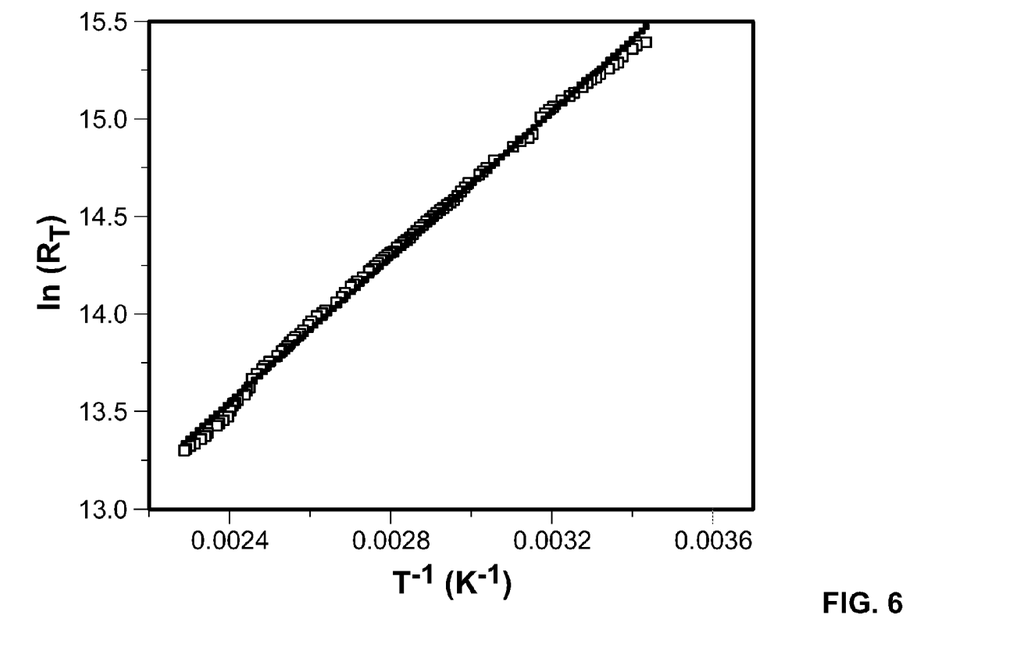
FIG. 6 is a plot showing a linear fit between the log of the electrical resistance of a graphene film as a function of the inverse of the temperature of the graphene film, the graphene film being an embodiment of the present invention.

The temperature-dependence performance of a printed graphene temperature sensor according to an embodiment of the present invention is shown in FIG. 5. The resistance of the graphene film decreases significantly with increased temperature. Referring to FIG. 6, the following equation was used to model the observed temperature-dependence as a negative temperature coefficient (NTC) behavior:

$$R_T = R_0 \exp\left(B\frac{(T_0 - T)}{T \cdot T_0}\right)$$

where $R_T$ is the electrical resistance as a function of temperature (T), B is the material constant and a measure of temperature sensitivity, and $R_0$ is the resistance at the reference temperature ($T_0$=298 K). By data fitting, B was determined to have a value of 1860 K in the temperature range of 298 to 358 K with the respective resistance changes from $4.4 \times 10^6$ to $2.4 \times 10^6 \Omega$. This B value is close to that of the conventional metal oxide ceramic NTC materials. The temperature coefficient of resistance ($\alpha$) was also used as another measure of temperature sensitivity where $$\alpha = R^{-1} \cdot \frac{dR}{dT}.$$

The value of $\alpha$ for exemplary graphene films of the present invention was determined to be $-0.0148$ K$^{-1}$ at 298 K, which is comparable with $\alpha$-values reported for other graphene films, such as chemically-reduced graphene oxide sheets and metal-diffused graphene oxide sheets. Also, the $\alpha$-value of exemplary graphene films of the present invention is about three orders of magnitude higher than that of carbon nanotubes.

Figure 7:
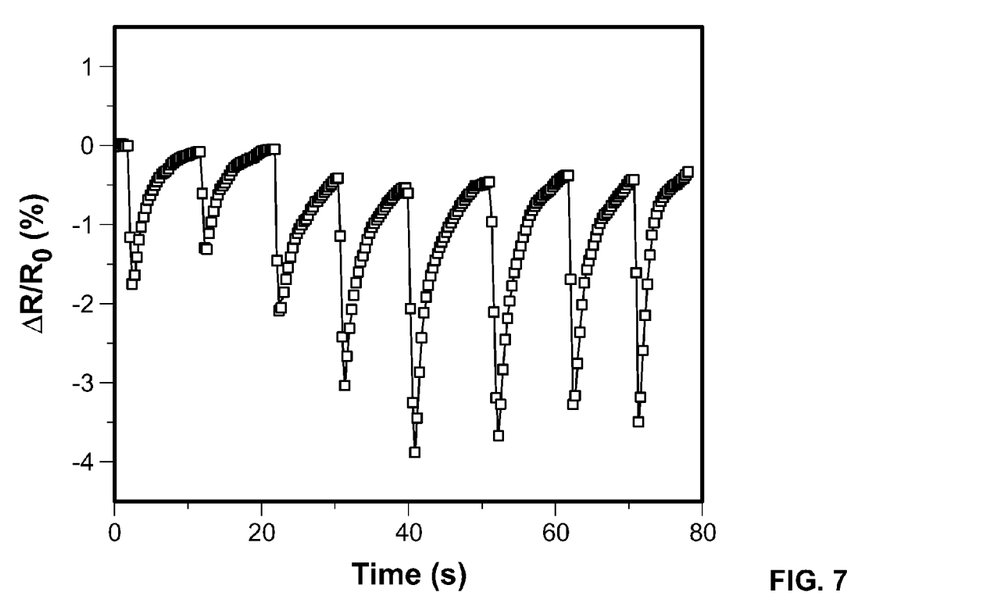
FIG. 7 is a plot showing the changes in relative electrical resistance of a graphene film prepared according to an embodiment of the present invention in response to repeated contact with a human fingertip.

The temperature-sensing function of the graphene film of the present invention was evaluated by lightly tapping the film with a human finger (at the temperature of the human body) in the ambient room environment. The repeated taps resulted in the resistance decreases shown in the FIG. 7. In contrast, no change in resistance was observed when the film was tapped with other objects that were in thermal equilibrium with the room environment (not shown).

The response time of the graphene film to temperature changes resulting from touching the film with a finger tip was about 0.5 seconds, and the recovery time to its initial resistance value upon removing the finger tip was about 10 seconds. In comparison, a typical response time for warming a conventional NTC metal oxide material is more than 10 seconds, suggesting an order-of-magnitude faster temperature-sensing function of the graphene film.

Figure 8:
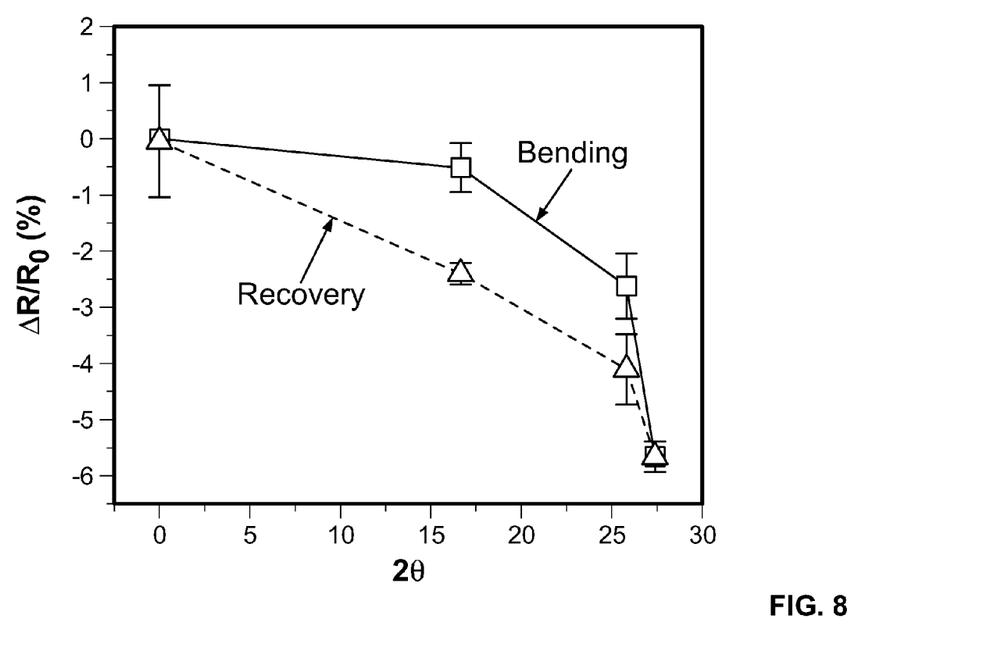
FIG. 8 is a plot showing the change of electrical resistance with respect to mechanical bending of a graphene film prepared according to an embodiment of the present invention.

The mechanical stability of the graphene film of the present invention upon bending is shown in FIG. 8, where an overall decrease of R of 5.6% was not achieved until the film was bent to $2\theta=27.4°$. These observations indicated that the effect of slight substrate flexing during tapping on the resistance of the graphene film was much smaller than that of warming the graphene film with the finger tip. Graphene film was constructed on the flexible substrate, therefore any change in the degree of bending of the substrate would lead to changes in the electrical resistance and one can use the correlation to develop the mechanical sensor.

Figure 9:
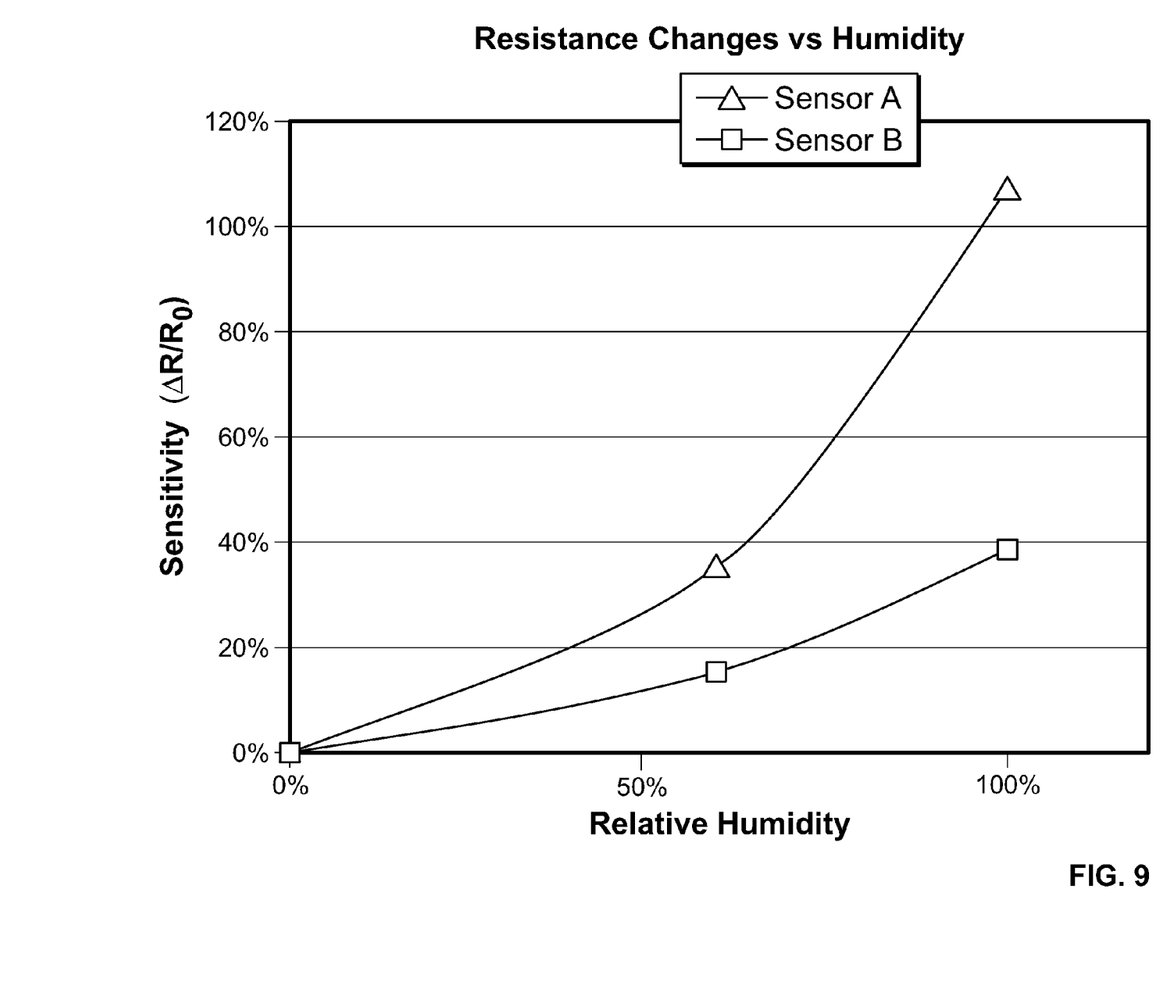
FIG. 9 is a plot showing the change of electrical resistance with respect to relative humidity in the environment of a graphene film prepared according to an embodiment of the present invention.
Figure 10:
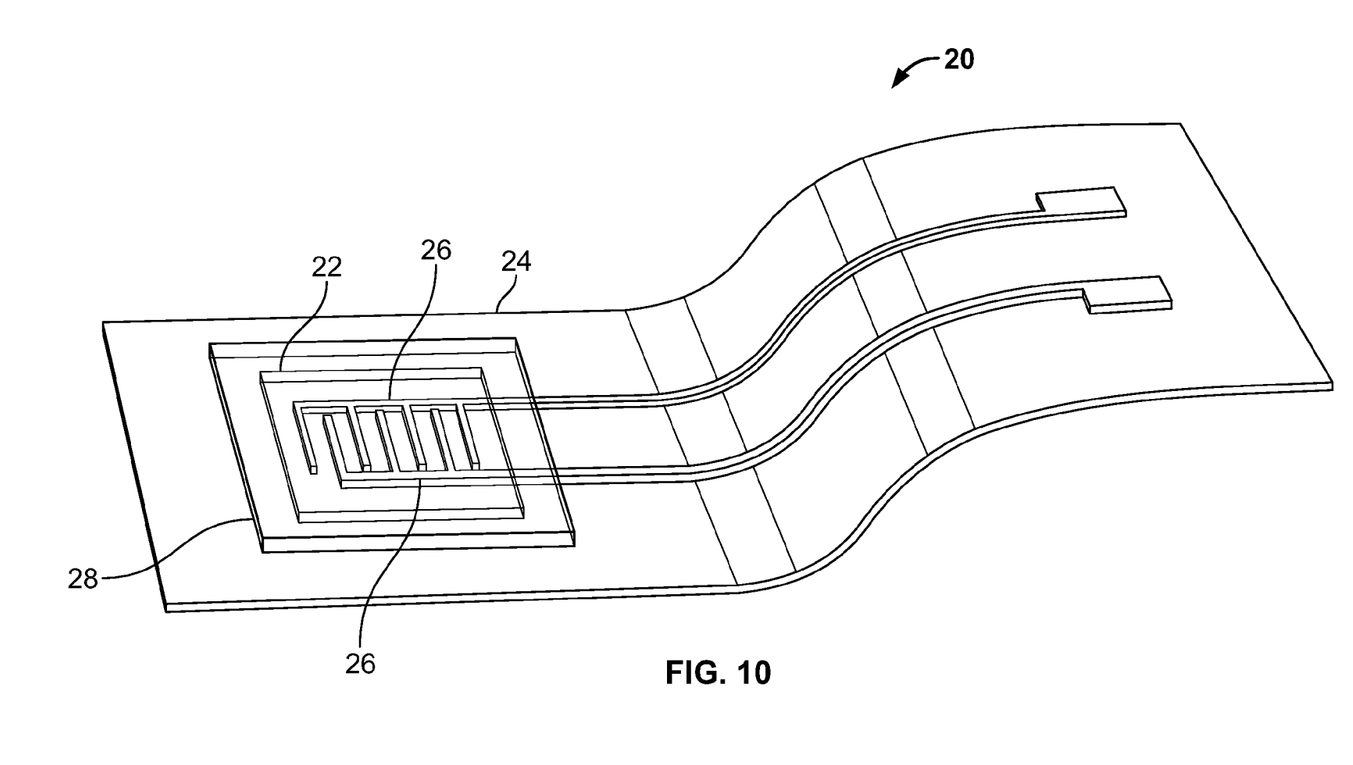
FIG. 10 is a schematic drawing of a design for a graphene film sensor according to an embodiment of the present invention.

Turning to FIG. 9, the humidity sensing function of a graphene film made according to the present invention was evaluated by constructing a sensor as later described with respect to FIG. 10, and measuring the changes in the electrical resistance of the sensor during exposure to different relative humidities in the environment of the sensor. The sensor was first dried overnight in an oven at 70° C. to remove excess water inside the sensor before the measurements of the electrical resistances of two different sensors (i.e., sensors A and B) were recorded at three relative humidity levels (i.e., 1%, 60% and 100% relative humidity) in the environment if the sensor. The sensitivity of the sensor to changes in humidity was calculated based on the changes of electrical resistance after normalizing to a relative humidity level at 1% ($R_0$). It was found that the resistances of both sensors increased with respect to higher relative humidities. Sensor A showed increases in resistance of 36% and 107% at relative humidities of 60% and 100%, respectively. Sensor B showed increases in resistance of 15% and 39% at relative humidities of 60% and 100%, respectively. It was also observed that the resistance sensor took no more than two minutes to stabilize when the sensor was exposed to the humid environment.

As demonstrated by the foregoing exemplary embodiments of the invention, inkjet-printed graphene has properties useful in fabricating temperature sensors having fast response times. FIG. 10 is a schematic drawing of a design for a graphene film temperature sensor 20 according to an embodiment of the present invention. Referring to FIG. 10, a graphene film 22 is inkjet-printed on the surface of an electrically insulating substrate 24 (e.g., Kapton® polyimide membrane) over a cross-finger, inter-digitized configured current collector 26. The current collector 26 may be formed from an electrically-conductive material (e.g., silver) and may be applied to the substrate 26 as a suspension of nanoparticles. Polymeric materials, including those suitable for use as the substrate 26, are often hydrophobic, and may resist adhesion of a water-based graphene oxide ink, such as those which may be used in embodiments of the present invention. In such cases, the substrate material may be pretreated to improve the adhesion and wetting behavior of the ink droplets. For example, a Kapton® polyimide substrate may be pretreated with $O_2$ plasma for 30 seconds prior to printing (e.g., using a plasma cleaner) to improve adhesion and wetting behavior of the ink. A suitable seal may be formed from a polymeric membrane (e.g., Kapton® FN polyimide film) that is heat-sealed to the electrically-insulating material over the graphene film 22. Adhesive bonding (e.g., by soft-lithographic techniques) may also be used to form a suitable seal. Routine experimentation based on ordinary knowledge of the materials' properties will be sufficient for most cases, but this area is also open to invention of novel materials and novel combinations of known materials.

It should be understood that the embodiments of the invention described herein are merely exemplary and that a person skilled in the art may make many variations and modifications without departing from the spirit and scope of the invention. All such variations and modifications are intended to be included within the scope of the invention as defined in the appended claims.

We claim:

1. A method of measuring temperature, comprising the steps of:
   providing a temperature sensor having an electrically-conductive current collector on a surface of an electrically-insulating substrate and a film including graphene in electrical communication with said current collector, wherein said film has an electrical resistivity and a negative temperature coefficient of resistance;
   measuring a reference electrical resistance of the film across said current collector when said film is at a reference temperature so as to obtain a data pair of the reference electrical resistance paired with the reference temperature;
   generating a mathematical correlation between the data pair of the reference electrical resistance paired with the reference temperature;
   measuring another electrical resistance of said film across said current collector when said film is at an unknown temperature;
   calculating a value for the unknown temperature from the another electrical resistance by the mathematical correlation.

2. The method of claim 1, wherein said step of measuring a reference electrical resistance is repeated at different reference temperatures so as to obtain a plurality of pairs of reference electrical resistances paired with reference temperatures, and the mathematical correlation of said generating step is generated from the plurality of data pairs of reference electrical resistances paired with reference temperatures.

* * * * *